(12) United States Patent
Li et al.

(10) Patent No.: US 12,293,838 B2
(45) Date of Patent: May 6, 2025

(54) SYSTEM FOR THE OVARIAN RESERVE FUNCTION ASSESSMENT OF SUBJECTS

(71) Applicant: GUANGZHOU KANGRUN BIOTECH CO., LTD, Guangdong (CN)

(72) Inventors: Rong Li, Beijing (CN); Huiyu Xu, Beijing (CN); Jie Qiao, Beijing (CN)

(73) Assignee: GUANGZHOU KANGRUN BIOTECH CO., LTD, Guangdong (CN)

( * ) Notice: Subject to any disclaimer, the term of this patent is extended or adjusted under 35 U.S.C. 154(b) by 600 days.

(21) Appl. No.: 17/413,182

(22) PCT Filed: Dec. 28, 2018

(86) PCT No.: PCT/CN2018/124766
§ 371 (c)(1),
(2) Date: Jun. 11, 2021

(87) PCT Pub. No.: WO2020/118790
PCT Pub. Date: Jun. 18, 2020

(65) Prior Publication Data
US 2022/0044822 A1 Feb. 10, 2022

(30) Foreign Application Priority Data
Dec. 12, 2018 (CN) .......................... 201811516206.4

(51) Int. Cl.
*G16H 50/30* (2018.01)
*A61B 5/00* (2006.01)
(Continued)

(52) U.S. Cl.
CPC .......... *G16H 50/30* (2018.01); *A61B 5/4325* (2013.01); *G01N 33/689* (2013.01); *G01N 33/76* (2013.01); *G06F 17/18* (2013.01)

(58) Field of Classification Search
None
See application file for complete search history.

(56) References Cited

U.S. PATENT DOCUMENTS

2016/0250296 A1* 9/2016 Arce ...................... A61K 38/24
600/33
2017/0107573 A1 4/2017 Beim

FOREIGN PATENT DOCUMENTS

| CN | 106168621 | 11/2016 |
| CN | 107257690 | 10/2017 |

(Continued)

OTHER PUBLICATIONS

Fauser et al., "Predictors of ovarian response: progress towards individualized treatment in ovulation induction and ovarian stimulation," Human Reproduction Update, 2007, vol. 14, No. 1, pp. 1-14.
(Continued)

*Primary Examiner* — Matthew G Marini
(74) *Attorney, Agent, or Firm* — Wenderoth, Lind & Ponack, L.L.P.

(57) ABSTRACT

A system and a method for assessing the ovarian reserve function of a subject. The system for assessing a subject's ovarian reserve function comprises: a data acquisition module configured to acquire data of the subject's age, anti-Müllerian hormone (AMH) level, follicle stimulating hormone (FSH) level, and antral follicle count (AFC); and an ovarian reserve function calculation module configured to calculate the above-mentioned information acquired in the data acquisition module, so as to work out the subject's probability of poor ovarian response (p). Further, the population is divided into four groups according to the interaction relationship between the predicted probability of poor ovarian response and the dose of ovulation stimulants, so as to (Continued)

divide the population with similar ovarian responses into one group.

5 Claims, 3 Drawing Sheets

(51) Int. Cl.
    *G01N 33/68*     (2006.01)
    *G01N 33/76*     (2006.01)
    *G06F 17/18*     (2006.01)

(56) References Cited

FOREIGN PATENT DOCUMENTS

| | | |
|---|---|---|
| WO | 2016/135221 | 9/2016 |
| WO | 2017/070258 | 4/2017 |

OTHER PUBLICATIONS

Li et al., "Anti-Müllerian hormone for prediction of ovarian response in Chinese infertile women undergoing IVF/ICSI cycles: a prospective, multi-centre, observational study," Reproductive Biomedicine Online, 2016, vol. 33, No. 4, pp. 506-512.

Extended European Search Report issued Jan. 4, 2022 in corresponding European Patent Application No. 18943028.3, 10 pages.

International Search Report (ISR) issued Aug. 27, 2019 in International (PCT) Application No. PCT/CN2018/124766.

Yang et al., "Effect of AMH, age, AFC, $E_2$ and FSH on the prediction of ovarian response and IVF outcome", Journal of Guangdong Pharmaceutical University, Oct. 31, 2016, vol. 32, No. 5, pp. 647-653, English abstract.

He, "The Clinical Study on the Relationship between the Predictors of Ovarian Reserve and Treatment Outcome of in Vitro Fertilization and Embryo Transfer", Chinese Master's Theses Full-text Database, Mar. 15, 2014, English abstract, cited in ISR.

Xia, "The Study on Ovarian Reserve and Ovarian Response Using Antrol Follicle Count and Anti-mullerian Hormone in in Vitro Fertilization-Embryo Transfer", Chinese Master's Theses Full-text Database, Aug. 15, 2015, English abstract, cited in ISR.

Huang et al., "Evaluation of ovarian reserve function and establishment of early warning model", Journal of Practical Obstetrics and Gynecology, May 31, 2017, vol. 33, No. 5, pp. 341-344, English abstract, cited in ISR.

\* cited by examiner

SYSTEM FOR THE OVARIAN RESERVE FUNCTION ASSESSMENT OF SUBJECTS

FIELD OF THE INVENTION

The present invention relates to a system for assessing the ovarian reserve function of a subject. The system can be used to assess the ovarian reserve function of the subject, to assess the fertility potential of the subject, and to assess whether the fertility potential of the subject is improved after corresponding treatments.

BACKGROUND OF THE INVENTION

The number of primordial follicles contained in the ovarian cortex is referred to as ovarian reserve. It reflects the ability of the ovaries to provide healthy ovums capable to be successfully fertilized, and is the most important evaluation indicator for women's ovarian function. Generally speaking, the more the number of primordial follicles, the better the quality and the higher the chance of conception.

Ovarian reserve function assessment can help women of childbearing age understand their own fertility status, so as to arrange their own birth plans. For women with a history of infertility, it can be used to predict the ovarian responsiveness of women of childbearing age, and provide references for clinical diagnosis and the formulation of treatment plans of infertility. At present, the main basis for diagnosing the decline of ovarian reserve function international and domestic is the prediction of poor ovarian response in Bologna criteria. Therefore, the indicator for evaluating ovarian reserve function is actually an indicator for predicting ovarian responsiveness.

Age factor is an important factor in ovarian reserve evaluation. The results of a study on age and IVF success rate show that the IVF success rate of women under 30 is about 26%, while the IVF success rate is only 9% when the age is 37 years and above.

Endocrine factor examination includes basal FSH level detection, AMH level detection and basal inhibin B level detection. Among them, (1) basal FSH detection: FSH is follicle stimulating hormone, secreted by the pituitary, and its main function is to promote the maturation of follicles. Basal FSH is also referred to as background FSH. In the first 0-3 days of the menstrual cycle, the initial stage of follicle growth, the granulosa cells in the follicle have not yet begun to secrete estrogen in a large quantity, and the feedback regulation of the pituitary gland and the ovary is at the initial stage. The FSH concentration measured at this stage is referred to as the basal FSH. Basal FSH directly reflects the secretory function of the ovary and is the most commonly used indicator for clinical evaluation of ovarian reserve function. The basal FSH of women with normal fertility is generally less than 10 IU/L, and the excessive basal FSH level reflects poor ovarian secretion function. FSH>12 IU/L indicates hypoovarianism, FSH>40 IU/L indicates ovarian failure, and in different laboratories, the values will be different. After the beginning of puberty, basal FSH will gradually increase with age. Studies have shown that the basal FSH level starts to rise ten years before menopause, and this is the age when the infertility rate stars to rise significantly. The results of multiple studies have shown that the basal E2 level decreases with the decline of ovarian function, and the basal LH level increases with age, but the change of basal FSH is earlier and more significant. In addition, the FSH:LH ratio can also be used to predict ovarian reserve function. (2) AMR (Anti-Müllerian hormone) level detection: AMR is a member of the transforming growth factor family. It is first secreted by the granulosa cells of primary follicles. The secretion at the stage of preantral follicle and small follicle (follicle diameter less than 4 mm) reaches its peak. Then the secretion volume gradually decreases. When the diameter of the follicle is greater than 8 mm, the secretion stops. Therefore, the AMR level can reflect the number of follicles recruited during the menstrual cycle, and the decrease in the number of recruited follicles indicates a decrease in ovarian reserve, so AMR level can directly reflect ovarian reserve and is internationally recognized as the best serological indicator currently for predicting the ovarian responsiveness. Generally speaking, the higher the AMR level in women, the more follicles are recruited, the better the responsiveness to the ovarian stimulation, and the higher the IVF success rate. However, high serum AMR levels may be caused by other diseases such as polycystic ovary syndrome, which should be excluded with reference to the transvaginal ultrasound examination. (3) Inhibin B level detection. Inhibin B is secreted by granulosa cells of the small follicle in the ovarian cortex, and its secretion increases with GnRH and FSH stimulation. The secretion changes greatly during the menstrual cycle, and it often fails to faithfully reflect the ovarian reserve capacity. Therefore, the detection of Inhibin B level is not currently a routine method for ovarian function assessment.

Ovarian ultrasonography includes the detection of three aspects: the number of antral follicles, the ovarian volume and the ovarian stromal blood flow. The number of antral follicles refers to the total number of antral follicles in bilateral ovarians counted by transvaginal ultrasonography in the early follicular phase, which is a direct manifestation of ovarian reserve capacity. The diameter of antral follicles is 2-10 mm or 3-8 mm. A decrease in the number of antral follicles indicates poor response to ovarian stimulation and a decreased pregnancy rate. Studies have shown that the number of antral follicles is more effective than basal FSH detection in the prediction of IVF success rate. Ovarian stromal blood flow and ovarian volume are currently not commonly used methods for ovarian responsiveness prediction and ovarian reserve function assessment.

In the field of reproductive medicine, the purpose of ovarian reserve assessment is to predict ovarian responsiveness. At present, AMII level detection and antral follicle count (AFC) are internationally recognized as the best two indicators for predicting ovarian responsiveness. Basal FSH level detection is currently the most widely used ovarian reserve assessment indicator in the world. Age factor is also an important factor in evaluating ovarian reserve.

SUMMARY OF THE INVENTION

Screening of basal FSH level is the most commonly used method for ovarian reserve prediction. When the threshold of basal FSH level is set relatively high, the diagnostic specificity for hypoovarianism increases, while the sensitivity decreases. Counting the number of antral follicles with transvaginal ultrasound is fast, economical, and accurate. However, it is related to the doctor's experience and the equipment, and there are human factors. AMH is secreted by granulosa cells in the early follicular phase. It is the earliest and most direct indicator of the degree of granulosa cell aging, and is a potential research direction. However, some disease conditions may interfere with the results of AMH, and its application alone is still insufficient for accurate ovarian reserve function assessment. In short, none of the ovarian reserve indicators can be used alone to diagnose decreased ovarian reserve, and it needs to be further confirmed with reference to other methods.

As mentioned above, assessing the ovarian reserve function of a subject is a very important task for clinicians, etc. By evaluating the ovarian reserve function, the patient's ovarian responsiveness, an important clinical outcome in the process of ovulation-stimulating therapy, can be predicted. In the past, clinicians often made judgments using their own experience and according to the age, body mass indicators, endocrine factor levels and the number of antral follicles, etc., and there was a certain degree of subjectivity. Our system can accurately assess the quality of the ovarian reserve function of the subjects to be treated, so as to assist the clinician to formulate more targeted treatment plans in the subsequent treatment.

In summary, it is known that the determinant of ovarian responsiveness is ovarian reserve function. However, the inventor of the present application thinks backward and uses predicted ovarian responsiveness to evaluate ovarian reserve function. In addition, for a patient receiving treatment for infertility, from a clinical point of view, ovarian responsiveness is not only related to the basic conditions of the patient (age, basal FSH level, AMH level, and number of antral follicles, etc.) but also related to the dose of ovulation stimulants. The inventors of the application first obtained the predicted probability of poor ovarian response based on the basic conditions of the patient, and then based on whether the interaction between the predicted probability of poor response and the dose of ovulation stimulant was significant, the population is divided into groups, and those with similar poor response trends are divided into a same group. From a statistical point of view, whether a stratification analysis (i.e., grouping in this application) is required is also determined according to whether the interaction is significant.

Specifically, the present invention relates to the following:

1. A system for assessing the ovarian reserve function of a subject, comprising:
a data acquisition module configured to acquire data of the subject's age, anti-Müllerian hormone (AMH) level, follicle stimulating hormone (FSH) level, and antral follicle count (AFC); and
an ovarian reserve function calculation module configured to calculate the above-mentioned information acquired in the data acquisition module, so as to work out the subject's probability of poor ovarian response (p).

2. The system according to item 1, further comprising:
a grouping module, in which default ovarian reserve function grouping parameters are prestored, and the calculated probability of poor ovary response p is grouped according to the grouping parameters, into a group, so as to group the subject's ovarian reserve level into a group.

3. The system according to item 1 or 2, wherein:
in the ovarian reserve function calculation module, the dichotomous variables transformed from the data of the subject's age, the subject's anti-Müllerian hormone (AMH) level, the subject's follicle stimulating hormone (FSH) level, and the subject's antral follicle count (AFC) are used to calculate the subject's probability of poor ovarian response (p).

4. The system according to item 3, wherein:
in the ovarian reserve function calculation module, the receiver operating characteristic (ROC) curve is used to detect the cutoff points of the age, the anti-Müllerian hormone (AMH) level, the follicle stimulating hormone (FSH) level, and the antral follicle count (AFC), and according to the tangent point values of the cutoff points, the age, the anti-Müllerian hormone (AMH) level, the follicle stimulating hormone (FSH) level, and the antral follicle count (AFC) are transformed into dichotomous variables, thereby the dichotomous variables are used to calculate the probability of poor ovarian response (p).

5. The system of item 4, wherein:
the anti-Müllerian hormone (AMH) level refers to the anti-Müllerian hormone concentration in the venous blood of a female subject on the 2nd-4th day of menstruation, the follicle stimulating hormone (FSH) level refers to the follicle stimulating hormone concentration in the venous blood of a female subject on the 2nd-4th day of menstruation, and the antral follicle count (AFC) refers to the total number of visible follicles with diameters of 2-8 mm in the two ovaries on the 2nd-4th day of menstruation counted with transvaginal B-scan ultrasonography.

6. The system according to item 4 or 5, wherein:
The tangent point value of the age is 35 years old, the tangent point value of the anti-Müllerian hormone (AMH) level is 0.93 ng/ml, the tangent point value of the follicle stimulating hormone (FSH) level is 9.1 IU/L, and the tangent point value of the antral follicle count (AFC) is 8.

7. The system according to any one of items 1 to 6, wherein:
in the ovarian reserve function calculation module, a formula for calculating the subject's probability of poor ovarian response (p) is pre-stored, wherein the formula is fitted with dichotomous variables transformed from the data of the subject's age, the subject's anti-Müllerian hormone (AMH) level, the subject's follicle stimulating hormone (FSH) level, and the subject's antral follicle count (AFC) in an exiting database.

8. The system according to item 7, wherein:
the formula is the following formula 1:

$$p = \frac{1}{1 + e^{-(i + a*age + b*AMH + c*FSH + d*AFC)}} \quad \text{(Formula 1)}$$

wherein, p is a calculated parameter used to characterize the subject's ovarian reserve function, i is any numeric value selected from −1.786 to −0.499, a is any numeric value selected from 0.063 to 1.342, b is any numeric value selected from −2.542 to −1.056, c is any numeric value selected from 0.548 to 1.838, and d is any numeric value selected from −2.133 to −0.51, wherein preferably I=−1.143, preferably a=0.703, preferably b=−1.799, preferably c=1.193, and preferably d=−1.322.

9. The system according to any one of items 2 to 8, wherein:
the grouping parameter pre-stored in the grouping module are:
when the calculated subject's probability of poor ovarian response (p) is <5%, the grouping module determines that the subject's ovarian reserve function is good;
when 5%≤the calculated subject's probability of poor ovarian response (p) <20%, the grouping module determines that the subject's ovarian reserve function starts to decline;
when 20%≤the calculated subject's probability of poor ovarian response (p) <50%, the grouping module determines that the subject's ovarian reserve function declines significantly; and
when the calculated subject's probability of poor ovarian response (p) is ≥50%, the grouping module determines that the subject's ovarian reserve function is poor.

10. A method for assessing the ovarian reserve function of a subject, comprising:
a data acquisition step, in which the data of the subject's age, anti-Müllerian hormone (AMH) level, follicle stimulating hormone (FSH) level, and antral follicle count (AFC) are acquired; and
an ovarian reserve function calculation step, in which the data of the age, the anti-Müllerian hormone (AMH) level, the follicle stimulating hormone (FSH) level, and the antral follicle count (AFC) acquired in the above data acquisition step are used to calculate the subject's probability of poor ovarian response (p).

11. The method according to item 10, wherein:
in the grouping step, the calculated probability of poor ovarian response is grouped according to the default grouping parameters of the ovarian reserve function in the grouping step, so as to group the subject's ovarian reserve level.

12. The method according to item 10 or 11, wherein:
in the ovarian reserve function calculation step, the data of the subject's age, the subject's anti-Müllerian hormone (AMH) level, the subject's follicle stimulating hormone (FSH) level, and the subject's antral follicle count (AFC) are transformed into dichotomous variables, and the transformed dichotomous variables are used to calculate the subject's probability of poor ovarian response (p).

13. The method according to item 12, wherein:
in the probability of poor ovarian response calculation step, the receiver operating characteristic (ROC) curve is used to detect the cutoff points of the age, the anti-Müllerian hormone (AMH) level, the follicle stimulating hormone (FSH) level, and the antral follicle count (AFC), and according to the tangent point values of the cutoff points, the age, the anti-Müllerian hormone (AMH) level, the follicle stimulating hormone (FSH) level, and the antral follicle count (AFC) are transformed into dichotomous variables, thereby the model of the dichotomous variables is used to calculate the subject's probability of poor ovarian response (p).

14. The method according to item 13, wherein:
the anti-Müllerian hormone (AMH) level refers to the anti-Müllerian hormone concentration in the venous blood serum of a female subject on the 2nd-4th day of menstruation, the follicle stimulating hormone (FSH) level refers to the follicle stimulating hormone concentration in the venous blood serum of a female subject on the 2nd-4th day of menstruation, and the antral follicle count (AFC) refers to the total number of visible follicles with diameters of 2-8 mm in the two ovaries on the 2nd-4th day of menstruation counted with transvaginal B-scan ultrasonography.

15. The method according to item 13 or 14, wherein:
the tangent point value of the age is 35 years old, the tangent point value of the anti-Müllerian hormone (AMH) level is 0.93 ng/ml, the tangent point value of the follicle stimulating hormone (FSH) level is 9.1 IU/L, and the tangent point value of the antral follicle count (AFC) is 8.

16. The method according to any one of items 10 to 15, wherein:
in the ovarian reserve function calculation step, the pre-stored formula for calculating the subject's probability of poor ovarian response (p) is used for the calculation, wherein the formula is fitted with the dichotomous variables transformed from the data of the subject's age, the subject's anti-Müllerian hormone (AMH) level, the subject's follicle stimulating hormone (FSH) level, and the subject's antral follicle count (AFC) in a pre-existing database.

17. The method according to any one of items 10 to 16, wherein:
in the ovarian reserve function calculation step, the subject's probability of poor ovarian response (p) is calculated using the following formula 1, and according to the data of the age, the anti-Müllerian hormone (AMH) level, the follicle stimulating hormone (FSH) level, and the antral follicle count (AFC) that are acquired in the data acquisition step and have been transformed into dichotomous variables:

$$p = \frac{1}{1 + e^{-(i + a*age + b*AMH + c*FSH + d*AFC)}} \quad \text{(Formula 1)}$$

wherein, p is a calculated parameter used to characterize the subject's ovarian reserve function, i is any numeric value selected from −1.786 to −0.499, a is any numeric value selected from 0.063 to 1.342, b is any numeric value selected from −2.542 to −1.056, c is any numeric value selected from 0.548 to 1.838, and d is any numeric value selected from −2.133 to −0.51, wherein preferably I=−1.143, preferably a=0.703, preferably b=−1.799, preferably c=1.193, and preferably d=−1.322.

18. The method according to any one of items 11 to 17, wherein:
the pre-stored basis for grouping in the grouping module is:
when the calculated subject's probability of poor ovarian response (p) is <5%, the grouping module determines that the subject's ovarian reserve function is good;
when 5%≤the calculated subject's probability of poor ovarian response (p) <20%, the grouping module determines that the subject's ovarian reserve function starts to decline;
when 20%≤the calculated subject's probability of poor ovarian response (p) <50%, the grouping module determines that the subject's ovarian reserve function declines significantly; and
when the calculated subject's probability of poor ovarian response (p) is ≥50%, the grouping module determines that the subject's ovarian reserve function is poor.

Invention Effect

Ovarian reserve function assessment can help women of childbearing age understand their own fertility status, so as to arrange their own birth plans. For women with a history of infertility, it can be used to predict the ovarian responsiveness of women of childbearing age, and provide references for clinical diagnosis of infertility and the formulation of treatment plans. At present, the main basis for the diagnosis of decreased ovarian reserve function domestic and overseas is the Bologna criteria for the diagnosis of poor ovarian response. Therefore, the indicator for evaluating ovarian reserve function is actually an indicator for predicting ovarian responsiveness.

Specifically, in the present invention, the system for evaluating a subject's ovarian reserve function can be used to calculate a subject's probability of poor ovarian response firstly, so that the subject's ovarian reserve level can be grouped according to the probability of poor ovarian response,. Using the system of the present invention, the parameter (p) for predicting the subject's probability of poor ovarian response can be calculated, and the subject's ovarian reserve function is grouped according to the default grouping parameters of ovarian reserve function pre-stored in the system to determine the level of the ovarian reserve function, so that the ovarian reserve level can be assessed.

The inventors of the present application realize that ovarian responsiveness is closely related to ovarian reserve. The worse the ovarian reserve function, the higher the risk of poor ovarian response. Whether having high risk of poor ovarian response is often used clinically to assess the ovarian reserve function decline. The order of ovarian reserve from good to poor is the order of the probability of poor ovarian response from low to high. Ovarian responsiveness is also closely related to the dose of drugs. The grouping criteria are established according to whether the interaction between the predicted probability of poor ovarian response (predictor variable) and the starting dose of exogenous ovulation stimulant (Gn) (predictor variable) significantly affects the outcome variable of poor ovarian response, and based on this grouping criteria, the subject's ovarian reserve level is assessed.

Using the system and method of the present invention can accurately assess the quality of the ovarian reserve function of a subject to be treated, and can assist clinicians to formulate more targeted treatment plans in subsequent treatments. For ordinary women of childbearing age, especially those who want to give birth but are not sure when to give birth, it can help them assess their ovarian reserve function and formulate a reasonable birth plan.

The inventors of the present invention is the first to use the four indicators of AMH level on the 2nd-4th day of menstruation, age, level of FSH on the 2nd-4th day of menstruation, and AFC counted with transvaginal B-scan ultrasonography on the 2nd-4th day of menstruation, to assess ovarian reserve function.

The system and method of the present invention can quickly and accurately assess the subject's ovarian reserve level, which solves the problem of poor repeatability and lack of uniform criteria led by that the ovarian reserve function is assessed based on the doctor's experience and some simple tangent point values of the ovarian reserve indicators in the prior art.

BRIEF DESCRIPTION OF THE DRAWINGS

By reading the detailed description in the following preferred specific embodiments, various other advantages and benefits of the present application will become clear to those of ordinary skill in the art. The drawings in the specification are only used for the purpose of illustrating the preferred embodiments, and are not considered as a limitation to the application. Obviously, the drawings described below are only some embodiments of the present application. For those of ordinary skill in the art, other drawings can be obtained based on these drawings without creative work. Also, throughout the drawings, the same reference numerals are used to denote the same components.

DETAIL DESCRIPTION OF THE INVENTION

Hereinafter, specific embodiments of the present invention will be described in more detail with reference to the drawings. Although specific embodiments of the present invention are shown in the drawings, it should be understood that the present invention can be implemented in various forms and should not be limited by the embodiments set forth herein. On the contrary, these embodiments are provided to enable a more thorough understanding of the present invention and to fully convey the scope of the present invention to those skilled in the art.

It should be noted that certain words are used in the description and claims to refer to specific components. Those skilled in the art should understand that they may use different terms to refer to the same component. In the specification and claims, differences in terms are not used to distinguish components, but differences in functions of components are used as a criterion for distinguishing. Such as "comprise" or "include" mentioned in the entire specification and claims is an open term, which should be interpreted as "include but not limited to". That in the following description of the specification are preferred embodiments for implementing the present invention, but the description is based on the general principles of the specification and is not intended to limit the scope of the present invention. The protection scope of the present invention shall be subject to those defined by the appended claims.

In this application, the ovarian reserve refers to the number of primordial follicles contained in the ovarian cortex, which is called ovarian reserve. It reflects the ability of the ovaries to provide healthy ovums capable to be successfully fertilized, and is the most important evaluation indicator for women's ovarian function. Generally speaking, the more the number of primordial follicles, the better the quality and the more the chance of conception.

However, the number of primordial follicles cannot be evaluated non-invasively. It can only be evaluated by the number of follicles mobilized in each menstrual cycle. Too few follicles mobilized in the IVF-ET cycle (poor ovarian response), suggesting a decline in ovarian reserve.

The age factor is generally considered to be the most important factor in evaluating ovarian reserve. A study on age and IVF success rate shows that the IVF success rate of women under 30 is about 26%, while the IVF success rate is only 9% when the age is 37 years and above.

The mechanism of the decline of ovarian reserve capacity with age is as follows. (1) The number of follicles decreases. Primordial follicles appear after embryonic sex differentiation. At this time, the number of follicles is the largest. After puberty, the follicles start to develop and mature. With the completion of ovulation, a large number of follicles that are recruited but not ovulated atrophy and disappear to form corpus luteum. The number of follicles continues to decrease with increasing age: in humans, it's the most in 20-week-old embryos, which is about 6 million follicles. While in the neonatal period, it is reduced to 0.7-2 million, and in the puberty, it is about 40,000. At the beginning of the menopause, there're only more than 1,000 remained, and are finally depleted completely. (2) The quality of the ovum decreases. The quality of the embryo is mainly determined by the quality of the ovum. Older age can increase the probability of ovum cell aneuploidy, increase the risk of mitochondrial dysfunction, loss of ovum polarity, and epigenetic changes in ovum cells. (3) Endocrine factors. The hypothalamic-pituitary-ovarian axis regulates women's menstrual cycle and ovulation. Abnormal endocrine levels in this axis can lead to infertility. AMH and inhibin B are secreted by small follicles and they are direct manifestations of ovarian reserve capacity. With the increase of age, the ovarian reserve decreases, and the number of follicles capable to be recruited decreases, so the concentration of AMH and inhibin B secreted by them also decreases. Inhibin B can negatively regulate the secretion of FSH from the pituitary. The decrease of inhibin B level leads to the increase of FSH secretion in the luteal phase. The pre-increased FSH promotes the growth of new follicles and the secretion of E2, and ultimately shortens the menstrual cycle. Serum FSH level increase, inhibin B level decrease, and the sensitivity of follicles to FSH decrease suggest that the number of antral follicles capable to be recruited decreases. Menstrual cycle is a manifestation of ovarian reserve and fertility. Older age leads to shortened menstrual cycle, and menstrual cycle reduction of 2-3 days is a sensitive indication of aging of the reproductive system, suggesting that follicle growth initiates in advance (FSH level increases) and primordial follicle reserve decreases.

Several infertility factors involved in this application are defined as follows. Endometriosis is a common gynecological disease in women that is formed when active endometrial cells grow outside the endometrium. Endometrial cells should grow in the uterine cavity, but as the uterine cavity is connected with the pelvic cavity through the fallopian tube, the endometrial cells can enter the pelvic cavity through the fallopian tube to grow ectopic. The main pathological changes of endometriosis are periodic bleeding of the ectopic endometrium and fibrosis and ectopic nodules forming in the surrounding tissues. Dysmenorrhea, chronic pelvic pain, menstrual abnormalities and infertility are the main symptoms. Lesions can spread to all pelvic tissues and organs, and the most common are the ovaries, rectouterine pouch, uterosacral ligament, etc. It can also occur in the abdominal cavity, thoracic cavity, limbs and other places. Tubal infertility refers to that as the fallopian tube has an important role in transporting sperm, picking up ovums, and transporting fertilized ovums to the uterine cavity, obstruction or dysfunction of the fallopian tube becomes the main cause of female infertility. The cause of obstruction or dysfunction of the fallopian tube is acute or chronic inflammation of the fallopian tube. In addition, unexplained infertility is defined as that standard tests of tubal patency and semen analysis show it's normal, while there is a history of repeated pregnancy failures in a couple.

Continuous variables: in statistics, variables can be divided into two categories, continuous variables and categorical variables, according to whether the value of the variable is continuous. Variables that can be arbitrarily valued within a certain interval are called continuous variables, and their values are continuous. Two adjacent values can be divided infinitely (i.e. an infinite number of values can be taken). For example, specified dimension of a product part, the measured height, weight, and bust of a human body, etc. are continuous variables, the values of which can only be obtained by measurement or metering. Conversely, if the value of a variable can only be calculated with natural numbers or integer units, it is a discrete variable. For example, the number of enterprises, the number of employees, the number of equipment, etc. which can only be counted as the number of measurement units. The values of these variables are generally obtained by counting.

Categorical variables refer to variables such as geographic location, demographics, etc., and its function is to group survey respondents. Descriptive variables describe the difference between a certain customer group and other customer groups. Most categorical variables are also descriptive variables. Categorical variables can be classified into two categories: unordered categorical variables and ordinal categorical variables. Among them, unordered categorical variables refer to no difference in degree or order between the classified categories or attributes. They can be further classified into ① dichotomous variables, such as gender (male, female), drug reaction (negative and positive), etc.; ② polytomous variables, such as blood type (O, A, B, AB), occupation (worker, farmer, businessman, scholar, soldier), etc. While there is a degree difference between the categories of the ordinal categorical variables. Such as urine glucose test results are classified into −, ±, +, ++, +++; therapeutic effects are classified into cure, significant efficacy, improved, and ineffective. For ordinal categorical variables, it should first be grouped according to the rank order, the number of observation units in each group should be counted to form a frequency table of ordinal variables (of each grade), and the data obtained is called ordinal data.

Variable types are not static, various types of variables can be interconvertible according to the needs of research purposes. For example, the amount of hemoglobin (g/L) is originally a numerical variable. If it's classified by normal hemoglobin and low hemoglobin, it can be analyzed as dichotomous variable data; if it's classified into five grades: severe anemia, moderate anemia, mild anemia, normal, increased hemoglobin, it can be analyzed as ordinal data. Sometimes the categorical data can also be quantified. For example, the patient's nausea response can be represented as 0, 1, 2, and 3, and then it can be analyzed as numerical variable data (quantitative data).

The present invention relates to a system for assessing the ovarian reserve function of a subject, comprising:

a data acquisition module configured to acquire data of the subject's age, anti-Müllerian hormone (AMH) level, follicle stimulating hormone (FSH) level, and antral follicle count (AFC);

a ovarian reserve function calculation module configured to calculate the above-mentioned information acquired in the data acquisition module, so as to calculate the subject's probability of poor ovarian response parameter (p).

The present invention also relates to a system for assessing the ovarian reserve function of a subject, comprising:

a data acquisition module, configured to acquire data of the subject's age, anti-Müllerian hormone (AMR) level, follicle stimulating hormone (FSH) level, and antral follicle count (AFC);

a ovarian reserve function calculation module, configured to calculate the above-mentioned information acquired in the data acquisition module, so as to calculate the subject's ovarian reserve function parameter (p); and a grouping module, in which default ovarian reserve function grouping parameters are prestored, and the calculated probability of poor ovary response p is grouped according to the grouping parameters, so as to group the subject's ovarian reserve level.

In the ovarian reserve function calculation module, the above-mentioned four continuous variable data: the subject's age, the subject's anti-Müllerian hormone (AMH) level, the subject's follicle stimulating hormone (FSH) level, and the subject's antral follicle count (AFC) are transformed into dichotomous variables to calculate the subject's probability of poor ovarian response (p).

Anti-Müllerian hormone (AMH) is a hormone secreted by the granulosa cells of the small follicles of the ovary. A female baby in the fetal period begins to produce AMH at the age of 9 months. The more small follicles in the ovary, the higher concentration of the AMH; on the contrary, when the follicles are gradually consumed with age and various factors, the AMR concentration will also decrease, and the closer to menopause, the AMR gradually tends to zero.

Follicle Stimulating Hormone (FSH) is a hormone secreted by basophils in the anterior pituitary gland. It is composed of glycoproteins and its main function is to promote the maturation of follicles. FSH can promote the proliferation and differentiation of follicular granulosa cells, and promote the growth of the entire ovary. And when acting on the seminiferous tubules of the testis, it can promote sperm formation. FSH is secreted in pulses in the human body, and changes with the menstrual cycle in women. The determination of FSH in serum is of great significance for the diagnosis or treatment of infertility and endocrine diseases, such as understanding the pituitary endocrine function, indirectly understanding the functional status of the ovary, assessing the ovarian reserve and ovarian responsiveness, and formulating the dosage of ovulation stimulants.

Antral follicle count (AFC) refers to the number of all visible follicles with a diameter of 2-8 mm in two ovaries on the 2nd-4th day of menstruation. AFC can be obtained by measuring and counting follicles with ultrasound.

In the present invention, the level of anti-Müllerian hormone (AMH) refers to the concentration of anti-Müllerian hormone (FSH) in the venous blood serum samples of female subjects on the 2nd-4th day of menstruation; the level of Follicle Stimulating Hormone (FSH) refers to the concentration of follicle stimulating hormone in the venous blood serum samples of female subjects on the 2nd-4th day of menstruation; and the antral follicle count (AFC) refers to the number of all visible follicles with the diameter of 2-8 mm in the two ovaries counted with transvaginal B-scan ultrasonography on the 2nd-4th day of menstruation.

In the ovarian reserve function calculation module, the receiver operating characteristic (ROC) curve is used to detect the cutoff points of the age, the anti-Müllerian hormone (AMH) level, the follicle stimulating hormone (FSH) level, and the antral follicle count (AFC). The continuous variables are transformed into dichotomous variables, which are substituted into the categorical variable model to calculate the probability of poor ovarian response. And according to the grouping criteria, the ovarian reserve function is grouped to obtain the subject's ovarian reserve function.

Although in the prior art, some researchers have tried to use some of the above parameters for analysis, but it is a unexpected discovery that by using the receiver operating characteristic (ROC) curve to detect the cutoff points of the age, the anti-Müllerian hormone (AMH) level, the follicle stimulating hormone (FSH) level, and the antral follicle count (AFC), transforming the age, the anti-Müllerian hormone (AMH) level, the follicle stimulating hormone (FSH) level, and the antral follicle count (AFC) into dichotomous variables according to the tangent point values of the cutoff points, and substituting all the dichotomous variables into the categorical variable model to calculate the probability of the occurrence of poor ovarian response. By transforming the four variables above into dichotomous variables and using such dichotomous variables for data analysis can predict the subject's ovarian reserve function more accurately, and the stability of the model is better. Accurate assessment of the subject's ovarian reserve function can help clinicians to formulate a more effective regimen, and to assess more accurately whether the therapeutic regimen can effectively improve the subject's ovarian reserve function after a period of treatment.

In the present invention, the tangent point value of age is 35 years old, the tangent point value of anti-Müllerian hormone (AMH) level is 0.93ng/ml, the tangent point value of follicle stimulating hormone (FSH) level is 9.1IU/L, and the cut point value of the antral follicle count (AFC) is 8.

In the ovarian reserve function calculation module, a formula for calculating the subject's probability of poor ovarian response (p) is prestored, wherein the formula is fitted with dichotomous variables transformed from the data of the subject's age, the subject's anti-Müllerian hormone (AMH) level, the subject's follicle stimulating hormone (FSH) level, and the subject's antral follicle count (AFC) in an exiting database. And according to the grouping criteria, the condition of the subject's ovarian reserve function is grouped.

In the present invention, an existing database refers to a database composed of subjects who are receiving treatment or have previously received treatment and meet the following inclusion and exclusion criteria. There is no agreement on the sample size of the database. Of course, the larger the sample size of the database, the better. For example, 100 subjects, 200 subjects, 300 subjects, preferably 400 subjects or more, and more preferably 500 subjects or more can be used. In a specific embodiment, an existing database composed of 561 samples is adopted.

The above inclusion and exclusion criteria are respectively as follows. The inclusion criteria are: women between 20 and 45 years old, body mass indicator (BMI)≤30, six consecutive menstrual cycles of 25 to 45 days, the morphology of bilateral ovaries is normal assessed by vaginal ultrasonography, and the number of previous IVF/ICSI-ET cycles≤2. The exclusion criteria are: hydrosalpinx, unilateral ovary AFC>20, polycystic ovary syndrome, other untreated metabolic or endocrine diseases, previous surgery for ovaries or uterine cavity, intrauterine abnormalities, within the first 3 months of pregnancy, smoking, using oral contraceptives or other hormones within the previous two months, having previously undergone radiotherapy or chemotherapy, and couples receiving PGD (preimplantation embryo genetic diagnosis)/PGS (preimplantation genetic screening) genetic diagnosis.

When selecting database samples, subjects who can be included in the database need to meet the above inclusion criteria and the exclusion criteria at the same time.

The ovarian reserve function calculation module uses the following formula to calculate the parameter (p) for characterizing the subject's ovarian reserve function according to the data acquired in the data acquisition module:

$$p = \frac{1}{1 + e^{-(i + a*age + b*AMH + c*FSH + d*AFC)}} \quad \text{(Formula 1)}$$

Wherein, p is a calculated parameter for characterizing the subject's ovarian reserve function, i is any numeric value selected from −1.786 to −0.499, a is any numeric value selected from 0.063 to 1.342, and b is any numeric value selected from −2.542 to −1.056, c is any numeric value selected from 0.548 to 1.838, and d is any numeric value selected from −2.133 to −0.51, wherein most preferably I=−1.143, and most preferably a=0.703, most preferably b=−1.799, most preferably c=1.193, and most preferably d=−1.322.

Further, the grouping parameters (i.e., the default ovarian reserve function grouping parameters) pre-stored in the grouping module of the present invention is the basis for grouping ovarian reserve functions, which is established by using the existing data and on the basis of the regression analysis result (i.e., whether the interaction between the starting dose of exogenous ovulation stimulant (Gn) (predictor variable) and the predicted probability of poor ovarian response (predictor variable) is significant in predicting whether poor response actually occurs (outcome variable)]. Because from the perspective of statistical analysis alone, if the interaction item is not statistically significant, it indicates that there is no need for stratification analysis, that is, no need for further grouping. The grouping basis pre-stored in the grouping module is: when the calculated parameter (p) for characterizing the subject's probability of poor ovarian response<5%, the grouping module determines that the subject's ovarian reserve function is good; when 5%≤the calculated parameter (p) for characterizing the subject's probability of poor ovarian response<20%, the grouping module determines that the subject's ovarian reserve function starts to decline; when 20%≤the calculated parameter (p) for characterizing the subject's probability of poor ovarian response<50%, the grouping module determines that the subject's ovarian reserve function declines significantly; and when the calculated parameter (p) for characterizing the subject's probability of poor ovarian response≥50%, the grouping module determines that subject's ovarian reserve function is poor.

That is, in the present invention, it is known that the determinant of ovarian responsiveness is the ovarian reserve function. The inventor of this application thinks backwards and uses predicted ovarian responsiveness to assess the ovarian reserve function. In addition, from a clinical point of view, ovarian responsiveness is not only related to the patient's basic condition but also relates to the dose of ovulation stimulants. We first obtain the predicted probability of poor ovarian response based on the patient's basic condition, and then based on whether the interaction between the predicted probability of poor response and the ovulation stimulant dose is significant, the population is divided into groups, and those with similar poor response trends are assigned into the same group. The grouping basis is established by using the subjects in the existing database and on the basis of whether the interaction between the subjects' starting doses of ovulation stimulant Gn and the predicted poor ovarian response probabilities is significant. In the present invention, different grouping criteria are first tested. Combining the starting dose of Gn with the distribution of the incidence of the predicted poor response, a variety of grouping methods are tested in ascending order of grouping intervals. Through multiple fittings, it is found that the grouping method in the present invention is the best combination. With the predicted probability of poor response of 5-20% as a reference, the interaction of each group is significant.

In the present invention, the population is further divided into four groups according to the interaction between the predicted probability of poor ovarian response and the dosage of ovulation stimulants, in order to those with similar ovarian responses are assigned into the same group. Ovarian reserve function is a determinant of ovarian responsiveness, and the inventors of the present application retrodict the ovarian reserve function from the predicted probability of poor ovarian response. The lower the probability of poor ovarian response, the better the ovarian reserve function. Therefore, as the probability of poor ovarian response increases, the ovarian reserve function can sequentially: ovarian reserve function is good, ovarian reserve function starts to decline, ovarian reserve function declines significantly, and ovarian reserve function is poor or relatively poor.

EXAMPLE

In the example, the sample size is estimated first. The total sample size should be >553 people, and all couples are trying to get pregnant for at least 12 months.

According to the following inclusion and exclusion criteria, a total of 561 couples from the three reproductive medicine centers are included for the study, that is, 561 couples meeting the following inclusion and exclusion criteria are selected for the follow-up study.

The inclusion criteria are: women aged 20 to 45 years old, body mass indicator (BMI)≤30, six consecutive menstrual cycles of 25 to 45 days, normal ovarian morphology assessed by vaginal ultrasound examination, the number of previous IVF/ICSI-ET cycles is ≤2.

The exclusion criteria are: hydrosalpinx, unilateral ovary AFC>20, polycystic ovary syndrome, other untreated metabolic or endocrine diseases, previous surgery for ovaries or uterine cavity, intrauterine abnormalities, within the first 3 months of pregnancy, smoking, using oral contraceptives or other hormones within the previous two months, having previously undergone radiotherapy or chemotherapy, couples receiving PGD (preimplantation embryo genetic diagnosis)/PGS (preimplantation genetic screening) genetic diagnosis.

Controlled Ovarian Stimulation (COS) Treatment

Gn (i.e., human recombinant FSH) treatment is started on the 2nd or 3rd day of the menstrual cycle. The starting dose is selected based on the age, the BMI (i.e., the body mass indicator, a figure obtained by dividing the weight in kilograms by the height in meters squared, which is a commonly used international standard for measuring the fatness and health), and the FSH and AFC levels on the 2nd-4th day of menstruation. During the period of ovulation-stimulating, the starting dose of Gn was adjusted according to ultrasound observation and serum E2 level. GnRH antagonist treatment starts on the 5-7th day of stimulation when the diameter of the growing follicle is 10-12 mm. When at least 2 dominant follicles (diameter 18 mm) are visible by ultrasound, 5000-10000 IU of hCG is given to initiate the final oocyte maturation. Oocyte retrieval was performed 36 hours after hCG administration. 1-3 embryos are transplanted or cryopreserved. A progesterone support for the luteal phase is then provided.

Antral Follicle Count Measurement and Endocrine Determination

During the COS cycle, a transvaginal ultrasound scan is performed on all subjects on the 2nd-4th day of menstrual cycle, and all visible follicles with a diameter of 2-8 mm in both ovaries are counted for the antral follicle count (AFC). On the same day, venous blood sampling is performed for the detection of serum AMH on the 2nd-4th day of menstruation, serum FSH on the 2nd-4th day of menstruation, serum LH (luteinizing hormone) on the 2nd-4th day of menstruation and serum E2 (estradiol) on the 2nd-4th day of menstruation.

In the present example, the level of follicle stimulating hormone (FSH) on the 2nd-4th day of menstruation refers to the level of follicle stimulating hormone acquired by detecting the venous blood serum sample of a female subject on the second to the fourth day of menstruation. The level of estrogen (E2) on the 2nd-4th day of menstruation refers to the level of estrogen acquired by detecting the venous blood serum sample of a female subject on the second to fourth day of menstruation. The level of anti-Müllerian hormone (AMH) on the 2nd-4th day of menstruation refers to the level of anti-Müllerian hormone acquired by detecting the venous blood serum sample of a female subject on the second to the fourth day of menstruation. The level of luteinizing hormone (LH) on the 2nd-4th day of menstruation refers to the level of luteinizing hormone acquired by detecting the venous blood serum sample of a female subject on the 2nd-4th day of menstruation.

The serum samples are taken and frozen at −80° C. The sealed samples are stored at room temperature (15 to 30° C.) for no more than 24 hours. The sample collection is completed in the hospital where the patient visits, and then immunoassays are performed to avoid multiple freeze-thaw cycles. The measurements of FSH, LH, E2 and AMH are all performed by Access UniCel DxI 800 chemiluminescence system (Beckman Coulter Inc). The quality control of FSH, LH and E2 is provided by Bio-RAD Laboratories (Lyphochek Immunoassay Plus Control, trilevel), item number is 370, batch number is 40300. The quality control of AMR is provided by the Beckman AMR kit. For AMH, FSH and LH, the coefficient of variation of the three levels of high, medium and low is controlled to be less than 5%, and for estradiol, the coefficient of variation of the three levels of high, medium and low is controlled to be less than 10%.

Analysis Scheme

In the analysis of the example, the variables used for prediction include age, BMI, cause of infertility, the number of AFC counted with transvaginal B-scan ultrasonography on the 2nd-4th day of menstruation, the FSH level on the 2nd-4th day of menstruation, the AMH level on the 2nd-4th day of menstruation, the LH level on the 2nd-4th day of menstruation and the E2 level on the 2nd-4th day of menstruation. The set outcome variable is poor ovarian response. Among them, poor ovarian response is defined as less than 5 (i.e., 0-4) oocytes on the day of oocyte retrieval. The difference between the two groups is tested by t test, Wilcoxon test or chi-square test. Appropriate methods are adopted according to the difference of data.

First, a binary logistic regression model is used to select the important factors related to poor ovarian response. In order to make the model more adaptable (i.e., even after the change of data (population), it may still have a relatively good practical significance), we change the variables of the four continuous variable indicators relating to the prediction of poor ovarian using the ROC (receiver operating characteristic) curve method according to the cutoff points to transform the consecutive variables into dichotomous variables. The process will be described in detail below. Then logistic regression is used to rebuild the prediction model with dichotomous variables, and the predicted probability of poor ovarian response is calculated.

As mentioned above, in this example, a total of 561 couples participating in the GnRH antagonist cycle meet the above inclusion and exclusion criteria. The data of the 561 couples are collected, and the collected data are input into SAS software and R software for analysis. And the data in Tables 1 and 2 below are obtained. Table 1 shows the basic and clinical characteristics of the 561 couples related to the retrieved oocytes.

TABLE 1

Patient clinical and biological data related to the results of the retrieved oocytes

| Variable | Number of retrieved oocytes | | P value |
|---|---|---|---|
| | 0-4 (n = 69) | ≥5 (n = 492) | |
| Age, (year) | 37 (33-41) | 31 (28-35) | <0.001 |
| BMI | 22.0 (20.1-23.9) | 21.8 (19.9-23.9) | 0.7911 |
| Cause of infertility, n (%) | | | <0.001 |
| Male factor | 24 (34.8%) | 194 (39.4%) | |
| Endometriosis | 9 (13.0%) | 15 (3.0%) | |
| Tubal factor | 20 (29.0%) | 172 (35.0%) | |
| Unknown cause | 10 (14.5%) | 101 (20.5%) | |
| Others | 6 (8.7%) | 10 (2.0%) | |
| AMH, ng/ml on the 2nd-4th day of menstruation | 0.5 (0.2-0.9) | 2.6 (1.3-4.3) | <0.001 |
| Antral follicle counts (AFC) on the 2nd-4th day of menstruation | 5 (3.5-7.5) | 13 (9-17) | <0.001 |
| FSH, IU/L on the 2nd-4th day of menstruation | 10.7 (8.3-13.3) | 7.4 (6.0-9.4) | <0.001 |
| LH, IU/L on the 2nd-4th day of menstruation | 3.9 (2.4-5.2) | 3.9 (2.7-5.6) | 0.4977 |
| $E_2$, pmol/L on the 2nd-4th day of menstruation | 164 (111-209) | 154 (120-205) | 0.8846 |
| Starting dose of Gn (IU) | 300 (150-300) | 150 (150-300) | <0.001 |
| Total dose of Gn (IU) | 2400 (1613-3150) | 1950 (1425-2700) | 0.0058 |

Median, Quartile

According to the results in Table 1, there is no significant difference in BMIs, LH levels on the 2nd-4th day of menstruation, and E2 variables on the 2nd-4th day of menstruation. On the other hand, age, causes of infertility (infertilities in different classifications of causes are counted, and the chi-square test is used to calculate whether there is a statistical significance p<0.001, indicating that the cause of infertility is statistically significant for whether it is a poor response), serum AMH and FSH levels on the 2nd-4th day of menstruation, AFC levels, starting doses and total doses of Gn have important correlations with the retrieved oocytes. The p values are listed in Table 1.

The above software is used to perform multiple regression analysis on the above data to determine which factors are independent predictors of poor ovarian response after adjusting for related factors. The results are shown in Table 2. According to the results in Table 2, age, AMH level on the 2nd-4th day of menstruation, serum FSH level on the 2nd-4th day of menstruation, and AFC number on the 2nd-4th day of menstruation are significantly related to the probability of poor ovarian response, and their p values are 0.0056, 0.0044, 0.0195 and 0.0049, respectively.

TABLE 2

Multivariable analysis for identifying the independent predictors of poor ovarian response

| Variable | Parameter estimate | SD | Wald $\chi^2$ | P Value |
|---|---|---|---|---|
| Age | 0.0946 | 0.0341 | 7.69 | 0.0056 |
| BMI | −0.0235 | 0.0571 | 0.17 | 0.6808 |
| AMH on the 2nd-4th day of menstruation | −0.6696 | 0.2353 | 8.1 | 0.0044 |
| FSH on the 2nd-4th day of menstruation | 0.0905 | 0.0388 | 5.46 | 0.0195 |
| LH on the 2nd-4th day of menstruation | −0.0201 | 0.0945 | 0.05 | 0.8314 |
| $E_2$ on the 2nd-4th day of menstruation | 0.0026 | 0.0022 | 1.46 | 0.2273 |
| AFC | −0.1584 | 0.0563 | 7.91 | 0.0049 |
| Cause of infertility [male factor vs. tubal factor] | −0.0015 | 0.2931 | 0 | 0.996 |
| Cause of infertility[endometriosis vs. tubal factor] | 0.6511 | 0.4367 | 2.22 | 0.136 |
| Cause of infertility[unknown cause vs. tubal factor] | −0.6336 | 0.366 | 3 | 0.0834 |
| Cause of infertility[others vs. tubal factor] | 0.1252 | 0.5307 | 0.06 | 0.8134 |

Further, in order to provide more practical meaning, age, AMH, FSH and AFC are transformed into dichotomous variables by using the tangent point values of the ROC curves. Specifically, the ROC curve is used to determine the cutoff points of age, AMH, FSH, and AFC, and the tangent point values of the cutoff points are determined respectively. The results are shown in FIGS. 1 to 4. According to the results in FIGS. 1 to 4, the tangent point values of age, AMH, FSH, AFC are found to be 35 years old, 0.93, 9.1, and 8 respectively. It can be determined that the results of the four indicators are as follows: the tangent point values of AMR, FSH and AFC are 35 years old, 0.93ng/ml, 9.1IU/L and 8, respectively. Thus the ages are divided into ≤35 and >35, AMHs are divided into ≤0.93 and >0.93, FSHs are divided into ≤9.1 and >9.1, and AFCs are divided into ≤8 and >8. According to the above standard, age, AMR, FSH and AFC are transformed into dichotomous variables.

The four newly generated dichotomous variables as described above are regarded as X and whether it is a poor ovarian response is regarded as Y for the multivariable analysis predicting whether the ovarian response is poor. The estimated values of the parameters in the established model are shown in Table 3 below.

TABLE 3

Parameter values of the model established by multivariable analysis

| Item | Parameter value | 95% CI of parameter | Deviation | ChiSquare | Prob > \|t\| |
|---|---|---|---|---|---|
| Intercept | −1.143 | −1.786, −0.499 | 0.328 | 12.11 | 0.0005 |
| dichotomous variables of age [>35 vs ≤35] | 0.703 | 0.063, 1.342 | 0.326 | 4.64 | 0.0313 |
| dichotomous variables of AMH [>0.93 vs ≤0.93] | −1.799 | −2.542, −1.056 | 0.379 | 22.5 | <.0001 |
| dichotomous variables of FSH [>9.1 vs ≤.1] | 1.193 | 0.548, 1.838 | 0.329 | 13.15 | 0.0003 |
| dichotomous variables of AFC [>8 vs ≤8] | −1.322 | −2.133, −0.51 | 0.414 | 10.19 | 0.0014 |

The logistic prediction model finally established according to the data in Table 3 is:

$$p = \frac{1}{1 + e^{-(i + a*age + b*AMH + c*FSH + d*AFC)}} \quad \text{(Formula 1)}$$

According to the data in Table 3, it can be determined that the range of i is −1.786~−0.499, and most preferably I=−1.143.

The range of a is 0.063-1.342, most preferably a=0.703; the range of b is −2.542~−1.056, most preferably b=−1.799; the range of c is 0.548~1.838, most preferably c=1.193; and the range of d is −2.133~−0.51, most preferably d=−1.322.

Figure 1:
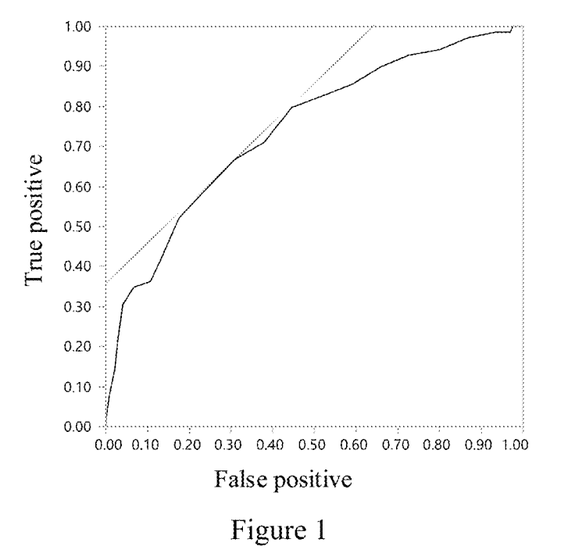
FIG. 1 ROC curve analysis of age variables.
Figure 2:
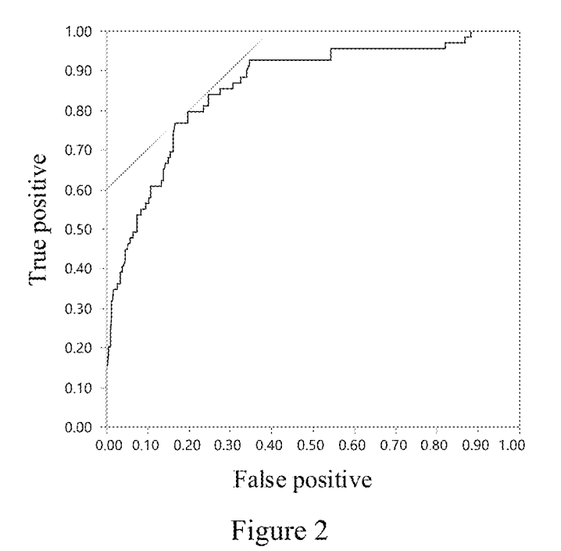
FIG. 2 ROC curve analysis of AMH level variables on the 2nd-4th day of menstruation.
Figure 3:
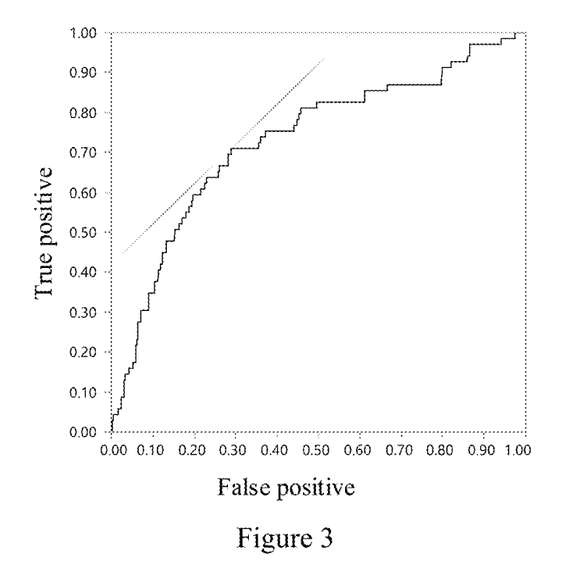
FIG. 3 ROC curve analysis of serum FSH level variables on the 2nd-4th day of menstruation.
Figure 4:
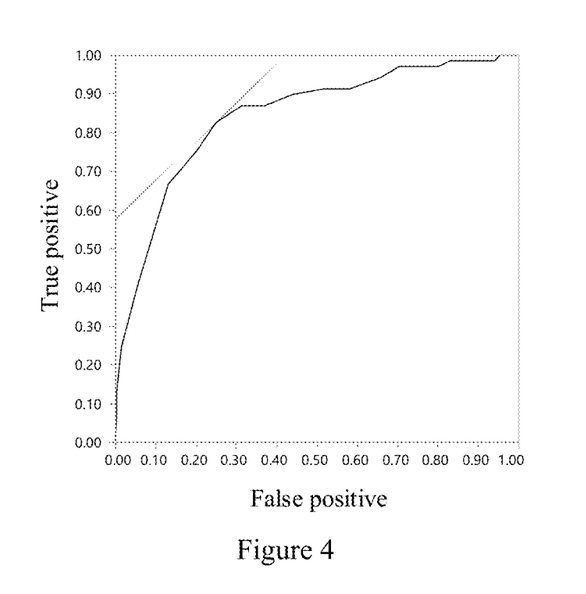
FIG. 4 ROC curve analysis of transvaginal B-scan ultrasonographic AFC level variables on the 2nd-4th day of menstruation.
Figure 5:
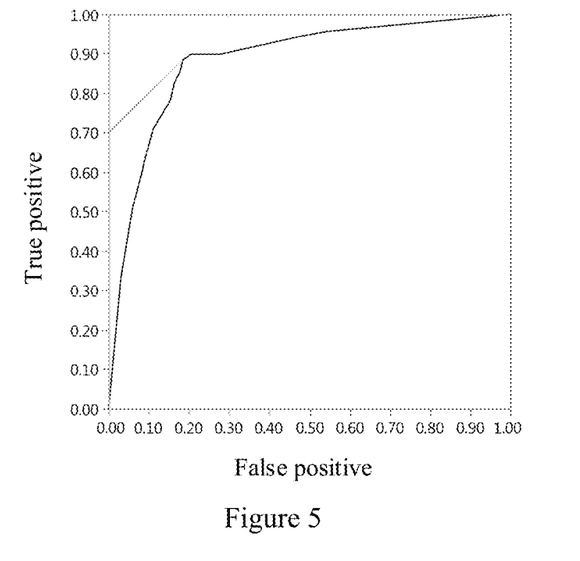
FIG. 5 ROC curve analysis of the model for assessing ovarian reserve function.

Further, according to the prediction model, the ROC curve is drawn. As shown in FIG. 5, the area under the ROC curve is 0.883. According to the results in FIG. 5, it can be seen that the model performs well in assessing the ovarian reserve function.

Therefore, according to the above formula one, the probability of a subject's poor ovarian response can be calculated based on the subject's age, concentration of anti-Müllerian hormone in the venous blood on the 2nd-4th day of menstruation, the concentration of follicle stimulating hormone in the venous blood on the 2nd-4th day of menstruation., and the number of all visible follicles with a diameter of 2-8 mm in the two ovaries on the 2nd-4th day of menstruation.

According to the calculated parameters of the probability of poor ovarian response, the population is grouped. In the present invention, different grouping methods are tried, and then through the interaction test, it is found that the interaction between the predicted low response probability and the starting dose of Gn is significant (p<0.05) only when the population is divided into the four groups: the predicted probability of poor response<5%, 5%≤the probability of poor response<20%; 20%≤the probability of poor response<50%; and 50%≤the probability of poor response.

Figure 6:
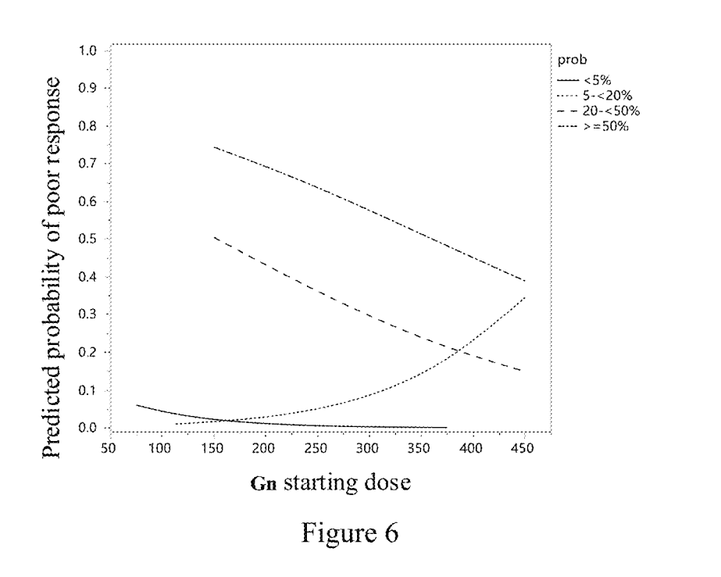
FIG. 6 Regression analysis showing the effect of the interaction between the starting dose of Gn and the predicted probability of poor ovarian response on the occurrence of poor ovarian response.

The specific method of the above interaction is as follows. Setting the interaction of the predicted probability of poor response calculated using formula 1 and the starting dose of Gn as X, and setting whether the response is poor as Y, multivariable logistic regression is performed. Thus the four main factors that affect the poor ovarian response are fixed, namely the binary variables AFC, AMH, FSH and age used in the present invention, and the impact of the dose change on whether the low response of the ovary occurs (that is, the predicted low response probability) is examined. The result of the interaction shows that the interaction model is significant P<0.05 when the population is divided into the four groups: the probability of poor response<5%, 5%≤the probability of poor response<20%; 20%≤the probability of poor response<50%; and 50%≤the probability of poor response. As shown in the interaction diagram (i.e., FIG. 6), after the establishment of the grouping criteria according to the above four groups, the interaction is significant. It indicates that such stratification (ie grouping) should be performed, because the trends of the probabilities of poor ovarian response in the four groups are different from each other.

Although the embodiments of the present invention are described above with reference to the drawings, the present invention is not limited to the above specific embodiments and application fields. The specific embodiments above are only illustrative, instructive, but not restrictive. With the inspiration of this specification and without departing from the scope of the protection of the claims in the present invention, those of ordinary skill in the art can also make various versions, which all belong to the protection of the present invention.

The invention claimed is:

1. A method for assessing an ovarian reserve function of a subject, comprising:
(A) a data acquisition step, in which the data of an age, anti-Müllerian hormone (AMH) level, follicle stimulating hormone (FSH) level, and antral follicle count (AFC) of the subject are acquired;
(B) an ovarian reserve function calculation step, in which the data of the age, the anti-Müllerian hormone (AMH) level, the follicle stimulating hormone (FSH) level, and the antral follicle count (AFC) acquired in the data acquisition step is used to calculate a probability of poor ovarian response (p) of the subject, wherein in the ovarian reserve function calculation step, a receiver operating characteristic (ROC) curve is used to detect cutoff points of the age, the anti-Müllerian hormone (AMH) level, the follicle stimulating hormone (FSH) level, and the antral follicle count (AFC), and according to tangent point values of the cutoff points, the age, the anti-Müllerian hormone (AMH) level, the follicle stimulating hormone (FSH) level, and the antral follicle count (AFC) are transformed into dichotomous variables, thereby the dichotomous variables are used to calculate the subject's probability of poor ovarian response (p) based on the following formula (1), $$p = \frac{1}{1 + e^{-(i + a*age + b*AMH + c*FSH + d*AFC)}} \quad \text{(Formula 1)}$$

wherein,
p is a calculated parameter used to characterize the ovarian reserve function of the subject,
i is any numeric value selected from −1.786 to −0.499,
a is any numeric value selected from 0.063 to 1.342,
b is any numeric value selected from −2.542 to −1.056,
c is any numeric value selected from 0.548 to 1.838, and
d is any numeric value selected from −2.133 to −0.51;

(C) grouping the subject based on the p value, wherein
(i) when p is <5%, the ovarian reserve function of the subject is good;
(ii) when 5% ≤p<20%, the ovarian reserve function of the subject starts to decline;
(iii) when 20%≤p<50%, the ovarian reserve function of the subject declines significantly; and
(iv) when p is ≥50%, the ovarian reserve function of the subject is poor; and
(D) an administering step of administering a starting dosage of an exogenous ovulation stimulant (Gn) to the subject, wherein the starting dosage is determined based on the p value and the grouping as defined in FIG. 6, wherein:
when p is <5%, the starting dosage of Gn is 75 to 375 IU;
when 5% ≤p<20%, the starting dosage of Gn is 115 to 450 IU;
when 20% ≤p<50%, the starting dosage of Gn is 150 to 450 IU; and
when p is ≥50%, the starting dosage of Gn is 150 to 450 IU.

2. The method according to claim 1, wherein:
the anti-Müllerian hormone (AMH) level refers to an anti-Müllerian hormone concentration in venous blood serum of a female subject on day 2-4 of menstruation, the follicle stimulating hormone (FSH) level refers to a follicle stimulating hormone concentration in venous blood serum of a female subject on the 2nd-4th day of menstruation, and the antral follicle count (AFC) refers to a total number of visible follicles with diameters of 2-8 mm in two ovaries on the 2nd-4th day of menstruation counted with transvaginal B-scan ultrasonography.

3. The method according to claim 1, wherein:
the tangent point value of the age is 35 years old, the tangent point value of the anti-Müllerian hormone (AMH) level is 0.93 ng/ml, the tangent point value of the follicle stimulating hormone (FSH) level is 9.1 IU/L, and the tangent point value of the antral follicle count (AFC) is 8.

4. The method according to claim 1, wherein:
in the ovarian reserve function calculation step, formula 1 is pre-stored for calculating the probability of poor ovarian response (p) of the subject and is used for the calculation, wherein formula 1 is fitted with the dichotomous variables transformed from the data of the age, the anti-Müllerian hormone (AMH) level, the follicle stimulating hormone (FSH) level, and the antral follicle count (AFC) of the subject in a pre-existing database.

5. The method according to claim 1, wherein:
i=−1.143,
a=0.703,
b=−1.799,
c=1.193, and
d=−1.322.

* * * * *